United States Patent
Vogt et al.

(10) Patent No.: US 12,285,338 B2
(45) Date of Patent: Apr. 29, 2025

(54) AUGMENTATION DEVICE, AUGMENTATION SYSTEM, AND IMPLANTATION METHOD

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 224 days.

(21) Appl. No.: 17/929,473

(22) Filed: Sep. 2, 2022

(65) Prior Publication Data
US 2023/0081855 A1    Mar. 16, 2023

(30) Foreign Application Priority Data
Sep. 10, 2021 (EP) .................................. 21195922

(51) Int. Cl.
*A61F 2/30* (2006.01)
*A61F 2/46* (2006.01)

(52) U.S. Cl.
CPC ........ *A61F 2/30734* (2013.01); *A61F 2/4603* (2013.01); *A61F 2002/30115* (2013.01); *A61F 2002/30217* (2013.01); *A61F 2002/30327* (2013.01); *A61F 2002/30332* (2013.01); *A61F 2002/30383* (2013.01); *A61F 2002/30545* (2013.01); *A61F 2002/30616* (2013.01); *A61F 2002/3069* (2013.01); *A61F 2002/30736* (2013.01)

(58) Field of Classification Search
CPC ........ A61F 2/30734; A61F 2002/30736; A61F 2002/30217; A61F 2002/30327; A61F 2002/30332; A61F 2002/30383; A61F 2002/30599
See application file for complete search history.

(56) References Cited

U.S. PATENT DOCUMENTS

| | | | | |
|---|---|---|---|---|
| 4,878,919 A | * | 11/1989 | Pavlansky | A61F 2/3662 623/23.18 |
| 2006/0241763 A1 | * | 10/2006 | Paul | A61F 2/4644 623/17.11 |
| 2008/0167722 A1 | * | 7/2008 | Metzger | A61F 2/30721 623/20.29 |
| 2011/0009974 A1 | * | 1/2011 | Blaylock | A61B 17/1764 623/20.32 |
| 2012/0296441 A1 | * | 11/2012 | Mikhail | A61F 2/2803 623/23.63 |
| 2014/0257499 A1 | * | 9/2014 | Winslow | A61F 2/4081 623/19.13 |

(Continued)

FOREIGN PATENT DOCUMENTS

| | | | | |
|---|---|---|---|---|
| CN | 205007078 U | * | 2/2016 | |
| DE | 102017004911 B3 | * | 5/2018 | ........... A61F 2/3609 |

*Primary Examiner* — Javier G Blanco
(74) *Attorney, Agent, or Firm* — Dicke, Billig & Czaja, PLLC (57) ABSTRACT

One aspect relates to an augmentation device comprising an annular cone surrounding a channel extending through the cone from a proximal cone end to a distal cone end of the cone. One aspect further relates to an augmentation system comprising such an augmentation device and an applicator, as well as an implantation method of an augmentation device using such an augmentation system.

11 Claims, 9 Drawing Sheets

(56) References Cited

U.S. PATENT DOCUMENTS

| | | | |
|---|---|---|---|
| 2015/0027920 A1* | 1/2015 | Riordan | B65D 25/282 |
| | | | 220/660 |
| 2018/0008416 A1* | 1/2018 | Vergari | A61F 2/389 |
| 2018/0200061 A1* | 7/2018 | Bauer | A61F 2/30767 |
| 2018/0271658 A1* | 9/2018 | Shi | A61F 2/30771 |
| 2019/0015212 A1* | 1/2019 | Marlow | A61F 2/3886 |
| 2021/0228366 A1* | 7/2021 | Heggs | A61F 2/30767 |

* cited by examiner

AUGMENTATION DEVICE, AUGMENTATION SYSTEM, AND IMPLANTATION METHOD

CROSS-REFERENCE TO RELATED APPLICATIONS

This application claims priority pursuant to 35 U.S.C. § 119(a) to European Application No. 21195922.6, filed Sep. 10, 2021, which application is incorporated herein by reference in its entirety.

FIELD

The invention relates to an augmentation device comprising an annular cone surrounding a channel extending through the cone from a proximal cone end to a distal cone end of the cone.

The invention further relates to an augmentation system comprising such an augmentation device and an applicator, as well as an implantation method of an augmentation device using such an augmentation system.

The subject matter of the invention is in particular an augmentation device for use in joint endoprosthesis surgery—in particular, revision joint endoprosthesis surgery.

The augmentation device according to the invention is suitable for strengthening or even partially replacing deformed bone tissue and thus enabling a secure and stable anchoring of a joint endoprosthesis—in particular, of a revision endoprosthesis—in a bone channel. In addition, the augmentation device according to the invention serves in particular for uniform introduction of force into the surrounding bone tissue during implantation of a joint endoprosthesis—in particular, a revision joint endoprosthesis.

BACKGROUND OF THE INVENTION

In orthopedic surgery, septic revisions of joint endoprostheses infected with micro-organisms must, unfortunately, be performed to a certain extent. In the process, the infected joint endoprostheses are explanted, and the infected or necrotic tissue is removed. This removal of infected/necrotic tissue is referred to as debridement. In this case, a substantial loss of bone tissue can occur in the region of the removed joint endoprosthesis—in particular, in the case of previously damaged bone tissue substance, e.g., as a result of osteoporosis—which can lead to problems in the anchoring of a revision joint endoprosthesis. In order to reinforce or partially replace the remaining bone tissue and to ensure the most uniform possible introduction of force into the remaining bone tissue during the use of the revision joint endoprosthesis, one possible treatment option consists in the use of an augmentation device in the form of a metal cone. To this end, the infected bone tissue is removed, and the cavity formed as a result is filled by inserting the augmentation device. The conical embodiment of the augmentation device serves to receive a shaft of a joint endoprosthesis or a revision joint endoprosthesis into a centrally-extending channel of the augmentation device and to anchor it there using, for example, bone cement. The augmentation device itself is designed such that it can be introduced into the cavity formed by the debridement. Such an augmentation device is described, for example, in patent specification U.S. Pat. No. 8,506,645 B2.

Usually, the imaging devices available on the market have a defined, predetermined size and cannot be adapted to the specific anatomical condition of the patient. Therefore, differently-sized augmentation devices are available on the market.

Patent specification EP 2 319 558 B1 describes an augmentation device whose size—in particular, its outer diameter—can be varied within certain limits. For this purpose, the augmentation device has an annular cone which has at least one, axially-extending bending joint. By means of the at least one joint, the cone can be compressed by a pressure acting from the outside, which reduces the outer diameter of the augmentation device.

When using joints—in particular, bending joints—it is considered disadvantageous for the adjustment of the size—in particular, of the outer diameter—of the augmentation device to be accompanied by a significant deformation of the augmentation device. As a result of adjusting the size, the augmentation device has a "kink" which makes it difficult to fit the augmentation device into the bone of the patient and can have a disadvantageous effect on the implantation of the joint endoprosthesis or the revision joint endoprosthesis. In addition, the size of the augmentation device can be adjusted only to a limited extent. It is not possible to adjust the axial extension of the augmentation device.

Therefore, an augmentation device is desirable which can be adjusted in size quickly and easily. It should be possible to adjust the size without the augmentation device being deformed. Furthermore, it should be possible to manually adjust the size during surgery in a few seconds, without using tools.

AIMS

It is an aim of the present invention to at least partially overcome one or more of the disadvantages resulting from the prior art.

In particular, an augmentation device is to be provided which can be quickly and easily adapted to the anatomical conditions of a patient. Furthermore, the augmentation device should not be deformed when the size is being adjusted.

It is a further aim of the invention to provide an augmentation system for quick and easy implantation of an augmentation device into a patient which avoids the limitations of conventional augmentation systems.

Another aim of the invention is to provide an implantation method with which an augmentation device can be implanted into a patient and which avoids the limitations of conventional implantation methods.

Preferred Embodiments of the Invention

A contribution to at least partial fulfillment of at least one of the aforementioned aims is achieved via the features of the independent claims. The dependent claims provide preferred embodiments that contribute to at least partial fulfillment of at least one of the aims.

A first embodiment of the invention is an augmentation device comprising an annular cone surrounding a channel extending through the cone from a proximal cone end to a distal cone end of the cone, characterized in that the cone is formed from a plurality of interconnected annular cone segments, wherein a cone segment outer diameter of the individual cone segments decreases from the proximal cone end to the distal cone end, and wherein the cone segments are designed to be separable from one another—in particular, in a non-destructive manner—so that the cone has an adaptable cone size.

In one embodiment of the augmentation device, the cone segments are designed to be reversibly separable from one another. This embodiment is a second embodiment of the invention, which is preferably dependent upon the first embodiment of the invention.

In one embodiment of the augmentation device, the cone segments are connected to one another in a form-fitting, force-fitting, or form-fitting and force-fitting manner. This embodiment is a third embodiment of the invention, which is preferably dependent upon the first or second embodiment of the invention.

In one embodiment of the augmentation device, the cone segments are connected to one another by means of a tongue-and-groove connection. This embodiment is a fourth embodiment of the invention, which is preferably dependent upon one of the preceding embodiments of the invention.

In one embodiment of the augmentation device, the cone segments each have a recess, a web, or a recess and a web, wherein the recess and the web of two cone segments adjacent in the cone interact in order to connect the two cone segments adjacent to one another in the cone—in particular, to connect them reversibly to one another. This embodiment is a fifth embodiment of the invention, which is preferably dependent upon one of the preceding embodiments of the invention.

In one embodiment of the augmentation device, the web and/or the recess are arranged on an inner surface of the cone segment. This embodiment is a sixth embodiment of the invention, which is preferably dependent upon the fifth embodiment of the invention.

In one embodiment of the augmentation device, the cone has a substantially smooth cone outer surface facing away from the channel. This embodiment is a seventh embodiment of the invention, which is preferably dependent upon one of the preceding embodiments of the invention.

In one embodiment of the augmentation device, the cone segments each have at least one guide, in order to reversibly connect the cone to an applicator. This embodiment is an eighth embodiment of the invention, which is preferably dependent upon one of the preceding embodiments of the invention.

In one embodiment of the augmentation device, the guide faces the channel so that the applicator can be reversibly connected to the cone by being introduced into the channel. This embodiment is a ninth embodiment of the invention, which is preferably dependent upon the eighth embodiment of the invention.

In one embodiment of the augmentation device, the cone segments are each designed in the form of a closed ring. This embodiment is a tenth embodiment of the invention, which is preferably dependent upon one of the preceding embodiments of the invention.

In one embodiment of the augmentation device, the cone segments comprise a polymer—in particular, a polymethyl methacrylate—a metal—in particular, titanium or tantalum—a metal alloy—in particular, a titanium alloy, a tantalum alloy, or a stainless steel—or a combination of the aforementioned. In particular, the cone segments consist of a polymer—in particular, a polymethyl methacrylate—a metal—in particular, titanium or tantalum—or a metal alloy—in particular, a titanium alloy, a tantalum alloy, or a stainless steel. This embodiment is an eleventh embodiment of the invention, which is preferably dependent upon one of the preceding embodiments of the invention.

A twelfth embodiment of the invention is an augmentation system comprising an augmentation device according to one of the preceding embodiments and an applicator, the applicator comprising a handle and a holding element connected to the handle, wherein the holding element is shaped such that, when the applicator is inserted into the channel, the holding element rests against an inner surface of the cone and thus reversibly connects the augmentation device and the applicator to one another.

In one embodiment of the augmentation system, the applicator can be inserted into the channel from the proximal cone end. This embodiment is a thirteenth embodiment of the invention, which is preferably dependent upon the twelfth embodiment of the invention.

In one embodiment of the augmentation system, on the holding element, holding element notches—in particular, step-like holding element notches—are formed which can be brought into engagement with cone notches—in particular, with stair-like cone notches—on the inner surface of the cone. This embodiment is a fourteenth embodiment of the invention, which is preferably dependent upon the twelfth or the thirteenth embodiment of the invention.

A fifteenth embodiment of the invention is an implantation method into a bone channel by means of an augmentation system according to one of the twelfth through fourteenth embodiments of the invention, comprising the following steps:
a. adapting the cone size of the augmentation device;
b. inserting the applicator into the channel of the augmentation device;
c. pressing the augmentation device into the bone channel by means of the applicator;
d. removing the applicator from the channel.

General

In the present description, range information also includes the values specified as limits. A specification of the type, "in the range of X to Y," with respect to a variable A consequently means that A can assume the values X, Y and values between X and Y. Ranges, delimited at one end, of the type, "up to Y," for a variable A correspond accordingly to a value Y and less than Y.

Some of the described features are linked to the term, "substantially." The term, "substantially," is to be understood as meaning that, under real conditions and manufacturing techniques, a mathematically exact interpretation of concepts such as "superimposition," "perpendicular," "diameter," or "parallelism" can never apply exactly, but can apply only within certain manufacturing-related error tolerances. For example, "substantially perpendicular axes" enclose an angle of 85 degrees to 95 degrees relative to one another, and "substantially equal volumes" include a deviation of up to 5 vol %. A "device consisting substantially of plastic" comprises, for example, a plastic fraction of ≥95 to ≤100 wt %. A "substantially complete filling of a volume B" comprises, for example, a filling of ≥95 to ≤100 vol % of the total volume of B.

The terms, "proximal" and "distal," merely serve to designate the spatially opposite ends of the augmentation device, of the cone, or of other structural units of the augmentation device and of the augmentation system, and do not allow any conclusions to be drawn about the orientation of the augmentation device implanted into a human body. "Distal to . . . " and "proximal to" or similar formulations accordingly express only the spatial arrangement of two structural units of the augmentation device and of the augmentation system relative to one another.

DETAILED DESCRIPTION

A first subject matter of the invention relates to an augmentation device comprising an annular cone surrounding a channel extending through the cone from a proximal cone end to a distal cone end of the cone, wherein the cone is formed from a plurality of interconnected annular cone segments, wherein a cone segment outer diameter of the individual cone segments decreases from the proximal cone end to the distal cone end, and wherein the cone segments are designed to be separable from one another so that the cone has an adaptable cone size.

The augmentation device has an annular cone. A cone is a conical—in particular, frustoconical—shaped component having a proximal cone end and a distal cone end axially opposite the proximal cone end, wherein a cone outer diameter decreases from one cone end to the other cone end—in this case, from the proximal cone end to the distal cone end.

The cone is annular or, in other words, tubular. As a result, the cone surrounds a channel which extends axially through the cone from the proximal end to the distal end. The channel is formed by an inner surface of the cone. The term, "annular," comprises, in an axial plan view of the cone segments, bodies having a circular, elliptical, angular, e.g., quadrilateral, pentagonal, or hexagonal, and irregular circumference, wherein bodies with an elliptical circumference are preferred, as they can be better implanted into a patient—in particular, into a bone channel of a patient.

The channel serves to receive and fix a shaft of a joint endoprosthesis or of revision joint endoprosthesis. For this purpose, the shaft of the corresponding endoprosthesis can be introduced into the channel—in particular, from the proximal end of the channel. The channel has a channel diameter which is determined by an inner diameter of a cone. In one embodiment, the inner diameter of the cone can be configured to be constant over the entire axial extension of the channel or of the cone. In a further embodiment, the cone diameter decreases concurrently with respect to the outer diameter of the cone from the proximal end of the cone to the distal end of the cone. In this embodiment, the cone has a cone wall thickness that is substantially equally thick over the entire axial extension of the cone.

The cone wall thickness can, for example, be in a range of 2 to 30 mm—preferably 2 to 15 mm, and more preferably 2 to 10 mm.

The cone is formed by a plurality of annular cone segments, i.e, by two or more, which are connected to one another. The cone can be formed, for example, from 2 to 20 cone segments—preferably from 4 to 15, and more preferably from 4 to 10, cone segments.

Each cone segment forms an annular section of the cone and a corresponding disk-shaped section of the channel of the cone. The cone segments are "stacked on top of one another" such that they form the cone.

The cone segments have a cone segment outer diameter, wherein the respective cone segment outer diameters of the individual cone segments differ. The cone segment with the largest cone segment outer diameter forms the proximal cone end, wherein the cone segment outer diameter of the cone segments adjoining in the distal direction always decrease further until finally the cone segment with the smallest cone segment outer diameter forms the distal cone end.

The cone segments have a cone segment outer diameter in a range of 20 to 60 mm—preferably 25 to 55 mm, and more preferably 30 to 55 mm. In cone segments which have an elliptical circumference in an axial plan view, the outer cone segment diameter means the length of the main axis, i.e., the longer of the axes extending through the center.

This allows a good adjustment of the cone size to the anatomical conditions of a patient.

The cone segments can be of different heights. For example, the height of the individual cone segments is in the range of 1 mm to 10 mm, and preferably in the range of 2 mm to 8 mm. This allows fast, effective, and, at the same time, sufficiently gradual adjustment of the axial extension of the augmentation device.

In one embodiment, the outer diameter of the cone segment is constant over the entire axial extension of the respective cone segment. In a further preferred embodiment, the cone segment outer diameter of the respective cone segment decreases linearly from a proximal end to a distal end of the cone segment, so that the cone segments connected to one another form a cone with a substantially step-free, i.e., substantially smooth, cone outer surface.

In one embodiment, the cone segments are roughened on a cone segment outer surface facing away from the channel or channel section or are formed with an open-pore structure in order to simulate spongious bone tissue.

The individual cone segments are designed to be separable from one another—in particular, in a non-destructive manner—so that the cone size—in particular, the maximum and/or the minimum outer diameter of the cone and the axial extension of the cone—can be varied. For example, the cone segment with the largest cone segment outer diameter can be separated from the remaining cone segments, which reduces the maximum cone outer diameter to the cone segment outer diameter of the cone segment with the second largest cone segment outer diameter and at the same time shortens the axial extension of the cone by the height of the removed cone segment. Further adjustments of the cone size are possible by further removal of additional cone segments at the proximal and/or distal cone end, until the cone ultimately consists only of a cone segment.

The separation of individual cone segments allows the cone size and thus the size of the augmentation device to be varied quickly and easily, even during surgery. The cone size can be adjusted over a wide range of anatomical conditions of a patient. At the same time, the original shape of the cone, with the exception of the cone outer diameter and the axial extension of the cone, is maintained. In particular, the adjustment of the cone size has no negative influence on the shape of the channel.

The cone segments may be connected to one another in different ways to form the cone. In one embodiment, the cone segments, after separation, can no longer be connected to one another without aids, such as, for example, an adhesive or a clip.

One embodiment of the augmentation device is characterized in that the cone segments can be reversibly separated from one another. The cone segments can therefore be connected to one another again after a separation. This allows a more flexible adjustment and "feeling the way" to the required cone size without the augmentation device becoming unusable after an initial incorrect adjustment of the cone size and having to be disposed of.

One embodiment of the augmentation device is characterized in that the cone segments are connected to one another in a form-fitting or force-fitting or form-fitting and force-fitting manner. This allows a simple, fast, and reversible separation of the individual cone segments by pulling apart or twisting apart. In addition, it is possible to separate the individual cone segments manually, i.e., without aids, such as scissors or forceps.

One embodiment of the augmentation device is characterized in that the cone segments are connected to one another by means of a tongue-and-groove connection. A tongue-and-groove connection connects the individual cone segments to one another in a form-fitting and/or force-fitting manner.

One embodiment of the augmentation device is characterized in that the cone segments each have a recess, a web, or a recess and a web, wherein the recess of a cone segment interacts with the web of a cone segment adjacent thereto in such a way that these two cone segments are connected to one another. In this case, the recess and the web form a form-fitting, a force-fitting, or a form-fitting and force-fitting connection. A web is an elevation on a proximal cone segment side and/or a distal cone segment side of a cone segment. A recess is a depression on a proximal and/or distal cone segment side of a cone segment. The web and recess of adjacent cone segments are coordinated with one another in such a way that the web can be accommodated in the recess. The web can completely fill the recess. In one embodiment, the web and/or the recess extend in a circular manner over the proximal and/or distal cone segment sides of the respective cone segment. In this case, the web or the recess encompasses the channel or the channel portion in a collar-like manner. In a further embodiment, the web and/or the recesses extend only in sections over the proximal and/or distal cone segment sides of the respective cone segment. In this case, the web can have a nub-like form, for example, so that the cone segments can be connected to one another as in a clamping building block.

In one embodiment, it is sufficient for the cone segment with the largest outer cone segment diameter to have a web or a recess on the distal cone segment side. It is likewise sufficient for the cone segment with the smallest cone segment outer diameter to have a web or a recess on the proximal cone segment side. The cone segments lying therebetween have a web or a recess both on the proximal and on the distal cone segment side. It is preferred that the webs and the recesses of the individual cone segments each be formed on the same side of the cone segment, e.g., all webs on the distal side of the cone segment and all recesses on the proximal side of the cone segment.

The web, the recess, or, if present, the web and the recess can be arranged at different regions on the proximal, the distal, or, if present, on the proximal and the distal cone segment sides, as long as the webs and recess of adjacent cone segments can interact in order to connect the cone segments to one another.

One embodiment of the augmentation device is characterized in that the recess, the web, or the recess and the web is or are arranged on an inner surface of the cone segment facing the channel or channel section. This means that the web or recess is formed on the boundary between the cone segment side and the inner surface of the cone segment. This allows simple assembly of the augmentation device—in particular, also to enlarge the augmentation device again after a previous separation of two cone segments.

One embodiment of the augmentation device is characterized in that the outer surface of the cone facing away from the channel is substantially smooth. The cone thus has a cone outer diameter which decreases linearly from the proximal cone end to the distal cone end. This allows the best possible adjustment of the cone size to the anatomical conditions of a patient.

The augmentation device can be implanted into a patient in different ways. For example, the augmentation device can be introduced—in particular, pressed—into a cavity provided for this purpose with bare hands.

In order to facilitate introduction into the desired position within a patient, it is preferred for the augmentation device to be able to be implanted into the patient with the aid of an applicator. An applicator is a device which can be reversibly connected to the augmentation device so that it can be introduced securely and easily at the desired location within the patient. After the introduction, the applicator can be quickly and easily released from the augmentation device. An applicator can, for example, be a gripping tool with which the augmentation device is gripped and inserted into a prepared cavity in the patient.

In order to facilitate the temporary, reversible connection of augmentation device and applicator, one embodiment of the augmentation device is characterized in that the individual cone segments each have a guide. The guides serve as a fastening point for the applicator on the augmentation device. For example, the applicator can be inserted at least in sections into the guide, so that the guide and the applicator are connected to one another in a form-fitting and/or force-fitting manner. The individual guides of the cone segments can be aligned relative to one another in such a way that a coherent cone guide is formed into which the applicator can be inserted.

The guides of the cone segments can be arranged on the outer surface of the cone segment or the inner surface of the cone segment facing the channel.

One embodiment of the augmentation device is characterized in that the guide faces the channel, i.e., is arranged on the inner surface of the cone segment. The applicator can thus be reversibly connected to the augmentation device by introduction into the channel—in particular, by introduction into the channel from the direction of the proximal cone end. At the same time, the outer surface of the cone remains uncovered by the applicator, which facilitates introduction of the augmentation device into a patient.

In one embodiment of the augmentation device, the cone segments have a gap such that the cone segments, and thus the cone, can be compressed according to the dimensions of the gap. In this embodiment, the cone segments are in the shape of an open ring. This allows fine adjustment of the cone size—in particular, of the outer diameter of the cone—without additional removal or addition of a cone segment at the proximal and/or distal cone end. The gap of a cone segment can, for example, be 1 to 10 mm wide. The gap can be protected by a tongue, covering the gap, on the corresponding cone segment.

One embodiment of the augmentation device is characterized in that the cone segments are each designed in the form of a closed ring, i.e., without a gap. Such cone segments have high structural integrity, which conveys a uniform application of force during implantation of a joint endoprosthesis or of a revision joint endoprosthesis.

The cone segments can comprise different materials or consist of different materials.

One embodiment of the augmentation device is characterized in that the cone segments comprise a polymer, a metal, a metal alloy, or a combination of the above—in particular, in that the cone segments consist of a polymer, a metal, a metal alloy, or a combination of the above. Examples of polymers are polymethyl methacrylate (PMMA) and polycarbonate, preference being given to polymethyl methacrylate (PMMA). Examples of metals are titanium, tantalum, aluminum, and iron. Examples of metal alloys are titanium alloys—in particular, $TiAl_6V_4$—tantalum alloys, and stainless steels—in particular, stainless steel 1.4404.

In order to better anchor the augmentation device in the patient, it may be advantageous for the outer surface of the cone to be roughened or formed with an open-pore structure. If the cone is formed from a polymer, it is preferred that the roughened or open-pore structure be coated with tantalum, titanium, a tantalum alloy, or a titanium alloy in order to promote growth of the bone tissue into the cone.

A further subject matter of the invention relates to an augmentation system comprising an augmentation device according to one of the preceding embodiments and an applicator. As described above, the applicator is a device which can be temporarily connected to the augmentation device so that it can be introduced securely and easily at the desired location within the patient. After the introduction, the applicator can be quickly and easily released from the augmentation device again. An applicator can, for example, be a gripping tool with which the augmentation device is gripped and inserted into a prepared cavity in the patient.

In order to operate the applicator, the applicator comprises a handle. The handle can be formed, for example, in the form of a rod, which can be encompassed by a user of the applicator with one hand. The handle serves for good transmission of force from the user, via the applicator, to the augmentation device during implantation.

The applicator has a holding element connected to the handle in order to reversibly connect the applicator to the augmentation device. The holding element is shaped and dimensioned such that it rests against the inner surface of the cone during insertion into the channel of the augmentation device.

In one embodiment, the holding element rests against at least two opposite locations of the inner surface of the cone in order to reversibly connect the applicator to the augmentation device. In a further embodiment, the holding element rests against more than two—in particular, against four—different locations of the inner surface of the cone. It is preferred that the more than two—in particular, four—locations be distributed as equidistantly as possible over the inner surface of the cone. This allows the most uniform transmission of force from the applicator to the augmentation device when implanting the augmentation device into a patient.

In order to transmit a force transmission from the applicator to the augmentation device as uniformly as possible to all cone segments, it is preferred that the holding element have an axial extension which corresponds at least to the axial extension of the cone. It is preferred that the holding element be in contact with all cone segments.

The augmentation device can have one of the guides described above on one, some, or all cone segments on the inner surface of the cone. This facilitates the reversible connection of augmentation device and applicator. For example, the holding element of the applicator is shaped like a rod, and the guide is shaped like a groove, so that the holding element can be inserted into the guide, and the augmentation device and applicator can be connected to one another in a form-fitting and/or force-fitting manner.

The applicator can be inserted into the channel of the augmentation device in different ways.

One embodiment of the augmentation system is characterized in that the applicator can be pushed into the channel from the proximal cone end. The channel end facing the proximal cone end can be wider than the opposite channel end facing the distal cone end, which simplifies the design of the applicator—in particular, of the holding element—and allows the use of a more robust applicator—for example, without moving parts. In addition, applicator access can thus be ensured over the entire axial extension of the cone.

The holding element can have different geometries in order to reversibly connect the applicator to the augmentation device—in particular, to the augmentation device on the inner surface of the cone. For example, the holding element can rest with a smooth surface against the augmentation device. In this case, it is preferred that the holding element and the inner surface of the cone have substantially the same incline, so that both components are in contact with one another over as long a distance as possible. A further possibility is that the inner surface of the cone and the holding element can be reversibly connected to one another via interlocking profiles. The guides described above can be designed as part of such a cone-side profile, or the guides described above are such a cone-side profile.

One embodiment of the augmentation system is characterized in that, on the holding element—in particular, on a part of the holding element facing the augmentation device—holding element notches—in particular, stair-like holding element notches—are formed which can be brought into engagement with cone notches—in particular, with stair-like cone notches—on the inner surface of the cone. The retaining element notches and the cone notches interact in a form-fitting manner, so that, during the application of force by the applicator to the augmentation device when the augmentation device is being implanted into a patient, the risk of the applicator sliding off the inner surface of the cone is reduced. The interaction of holding element notches and cone notches improves the reversible connection of applicator and augmentation device during implantation into a patient.

In this case, the cone notches can be formed as part of one of the guides described above, or the cone notches constitute a guide described above.

The holding element can be provided with latching hooks on a side opposite the handle in order to effectively prevent the cone segments from sliding off the holding element.

A further subject matter of the invention relates to a method for implantation into a bone channel by means of an augmentation device according to one of the preceding embodiments, comprising the following steps:
  a. adapting the cone size of the augmentation device;
  b. inserting the applicator into the channel of the augmentation device;
  c. pressing the augmentation device into the bone channel by means of the applicator;
  d. removing the applicator from the channel.

The cone size of the augmentation device can be adapted by removing and/or adding one or more cone segments at the proximal and/or distal cone ends. This allows both the adjustment of the maximum and minimum outer diameters of the cone as well as the axial extension of the cone.

In one embodiment, the initial augmentation device already has a suitable cone size, so that no adjustment is necessary, and step a. can be skipped.

In order to implant the augmentation device into a patient, the augmentation device and applicator are reversibly connected to one another. This is done by inserting the applicator into the channel of the augmentation device, so that the holding element of the applicator comes into contact with the inner surface of the cone. The cone size can be adjusted, if necessary, before or after the augmentation device and applicator are connected.

To introduce the augmentation device into the patient—in particular, into the bone channel of the patient—the augmentation device is arranged at the desired location, followed by an application of force to the augmentation device via the applicator. The application of force presses the augmentation device into the bone channel. In particular, the augmentation device is introduced into the bone channel with the distal end of the cone to the fore.

When the augmentation device is implanted at the desired location, the applicator is removed from the channel—in particular, by means of a pulling movement.

If desired, the cone size can, after introduction, be varied by adding or removing a cone segment—in particular, at the proximal end of the cone. For example, a cone segment protruding after the introduction into the bone channel can be removed.

The features disclosed for the augmentation device are also disclosed for the augmentation system and the augmentation method, and vice versa.

FIGURES

The invention is illustrated by way of example below by means of figures. The invention is not limited to the figures.

The following are shown.

DESCRIPTION OF THE FIGURES

Figure 1:
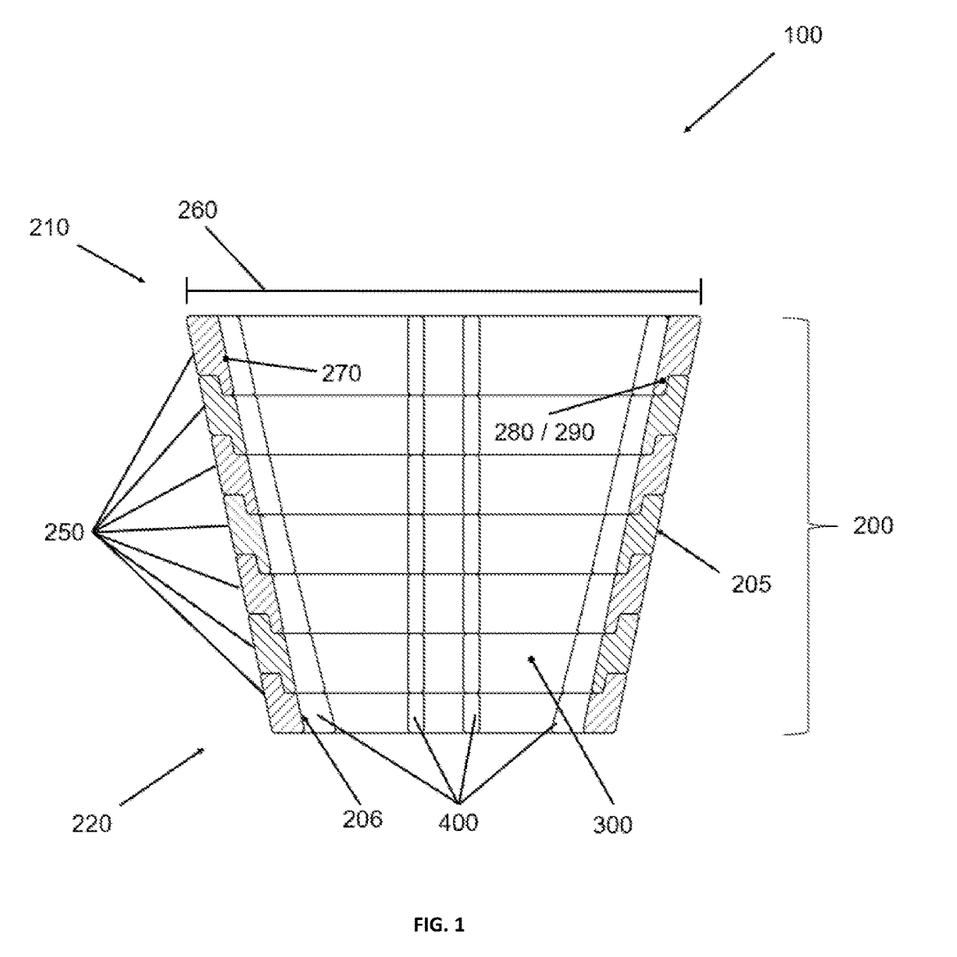
FIG. 1 a schematic longitudinal section of an augmentation device.

FIG. 1 shows a schematic longitudinal section of an exemplary embodiment of an augmentation device 100. The augmentation device 100 comprises an annular cone 200 with a proximal cone end 210 and a distal cone end 220 opposite the proximal cone end 210.

A channel 300 extends through the cone 200 from the proximal cone end 210 to the distal cone end 220.

The cone 200 itself is constructed from a plurality of—in this case, seven—annular cone segments 250 connected to one another. The cone segments 250 have differently-sized cone segment outer diameters 260 (drawn only for the cone segment 250 at the proximal cone end 210), wherein the cone segment at the proximal cone end 210 has the largest cone segment outer diameter 260, and the cone segment outer diameter 260 of the cone segment 250 arranged distally thereto decreases linearly up to the distal cone end 220, so that a cone outer surface 205 is formed to be substantially smooth, with the exception of the transitions from a cone segment 250 to a cone segment 250 adjacent thereto. The cone segment 250 at the distal cone end 220 has the smallest cone segment outer diameter 260. The individual cone segments 250 have a substantially smooth cone segment inner surface 270 (drawn only for the cone segment at the proximal cone end 210), so that the cone 200 composed of the cone segments 250 has a substantially smooth cone inner surface 206.

The cone segments 250 each have a substantially identical wall thickness, so that the channel 300, just like the cone 200, has its greatest extension at the proximal cone end 210, and the extension in the direction of the distal cone end continues to decrease. In a further embodiment, not shown, the channel has the same extension over the entire axial extension of the cone 200. In said embodiment, not shown, the individual cone segments 250 have different wall thicknesses, wherein the wall thickness is greatest at the proximal cone end 210 and continues to decrease in the direction of the distal cone end 220.

With the exception of the cone segment 250 at the distal cone end 220, all other cone segments 250 shown in this embodiment each have a circumferential web 290 on the inner surface 270 of the cone segment facing the channel 300, each of which interacts with a recess 280 of the respective distally adjacent cone segment 250 in a form-fitting and/or force-fitting manner, in order to connect the respective adjacent cone segments 250 separably to one another (drawn only for the cone segment 250 at the proximal cone end 210 and the cone segment 250 distally adjacent thereto). With the exception of the cone segment 250 at the proximal cone end 210, all other cone segments 250 shown in this embodiment have a circumferential recess 280 on the inner surface 270 of the cone segment facing the channel 300, each of which interacts with the webs 290 of the proximally adjacent cone segments 250, in order to connect the respective adjacent cone segments 250 to one another in such a way that they are separable from one another. In the embodiment shown, the cone segment 250 at the proximal cone end 210 has only one web 280, and the cone segment 250 at the distal cone end 220 has only one recess on the respective inner surface 270 of the cone segment in the embodiment shown. The cone segments distal to the proximal cone segment 250 and proximal to the distal cone segment 250 have both a recess 280 and a web 290 on the respective inner surfaces 270 of the cone segment.

In the embodiment of the augmentation device 100 shown, all cone segments 250 have a plurality of guides 400 (drawn only for the distal cone segment 250) in order to reversibly connect the augmentation device 100 to an applicator (not shown in FIG. 1). Each cone segment 250 has four guides 400, wherein one of the guides 400 is arranged centrally behind the drawing plane in the image, two of the guides 400 are illustrated in the drawing plane, and thus only half-illustrated, and one of the guides 400 is in front of the drawing plane and therefore not shown. The guides 400 are distributed uniformly over the inner surface 270 of the cone segment. Each guide 400 comprises two, rail-like elevations, so that an applicator (not shown in FIG. 1) can engage with corresponding counterparts between the elevations of a guide 400 in order to connect the augmentation device 100 and the applicator. The individual guides 400 of the cone segments 250 are oriented relative to one another in such a way that four, rail-like cone guides are formed on the inner surface 206 of the cone to which an applicator can be connected.

Figure 2:
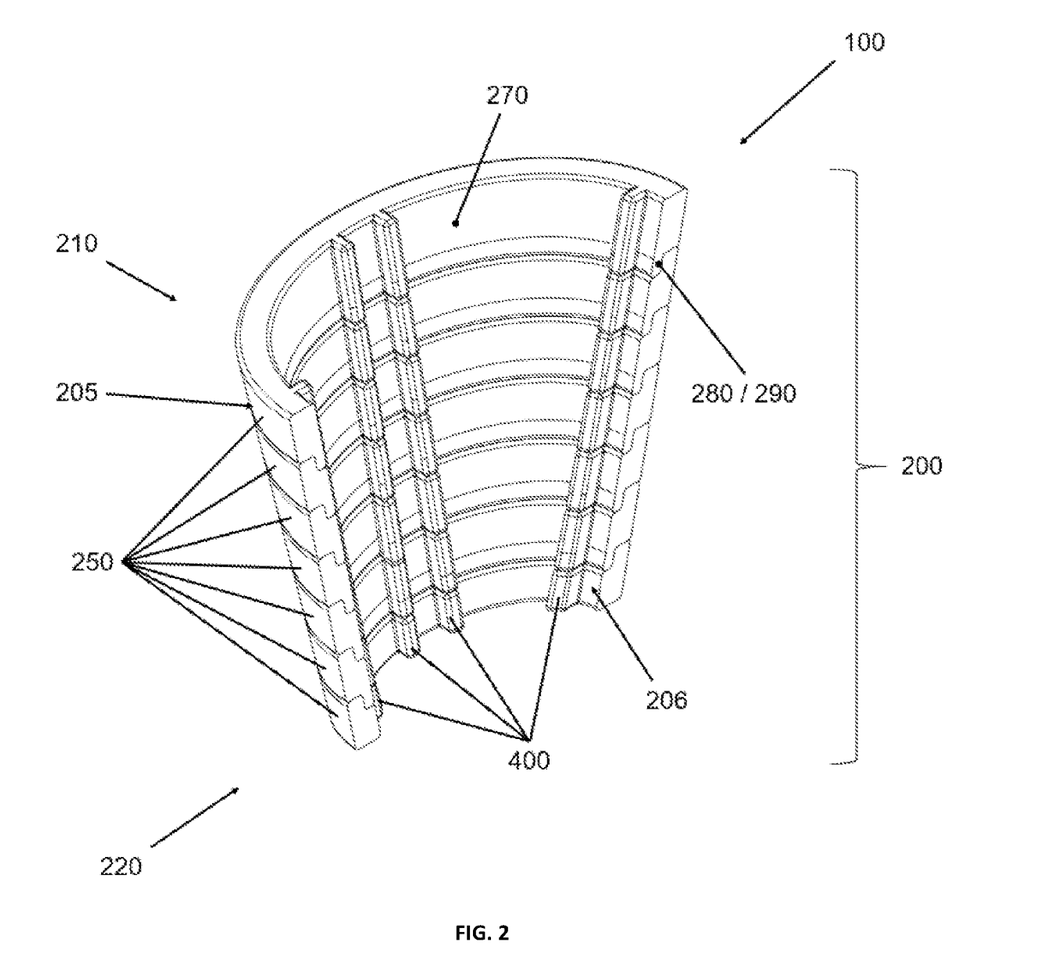
FIG. 2 the schematic longitudinal section of the augmentation device from FIG. 1 in a perspectival side view, FIG. 3 the augmentation device from FIGS. 1 and 2 in a perspectival side view, FIG. 4 a schematic longitudinal section of a second augmentation device, FIG. 5 the schematic longitudinal section of the second augmentation device from FIG. 4 in a perspectival side view, FIG. 6 a schematic longitudinal section of an augmentation system comprising the second augmentation device from FIGS. 4 and 5 and an applicator, FIG. 7 the schematic longitudinal section of the augmentation system from FIG. 6 in a perspectival side view, FIG. 8 the applicator from FIGS. 6 and 7 in a perspectival side view, and FIG. 9 a flowchart of an implantation method.

FIG. 2 shows the schematic longitudinal section of the augmentation device 100 from FIG. 1 in a perspective side view. To avoid repetition, reference is made to the above description of FIG. 1.

Figure 3:
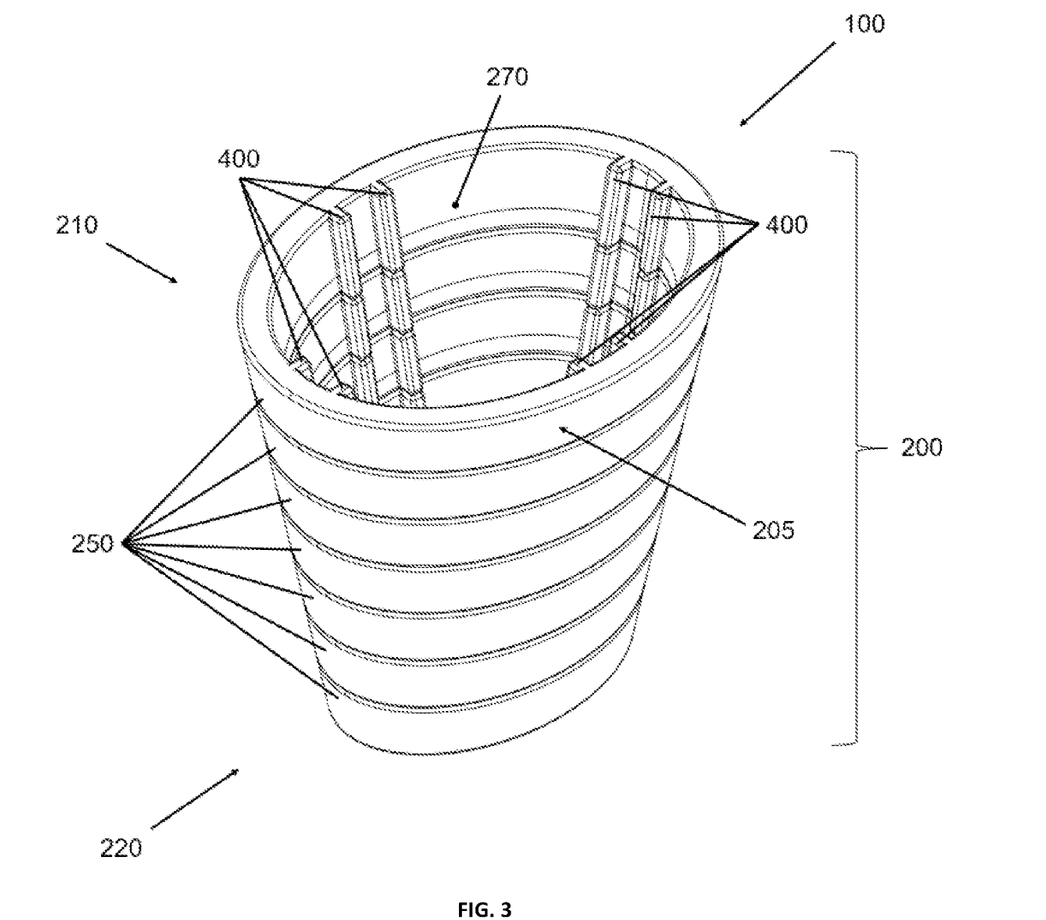

FIG. 3 shows the augmentation device 100 from FIGS. 1 and 2 in a perspectival side view. In the perspective side view, all four guides 400 are visible. Furthermore, it can be seen that the annular cone segments 250 have an elliptical design in an axial plan view. In the embodiment of the augmentation device 100 shown, the cone segments 250 are closed, i.e., without a gap.

To avoid repetition, reference is made to the above description of FIGS. 1 and 2.

Figure 4:
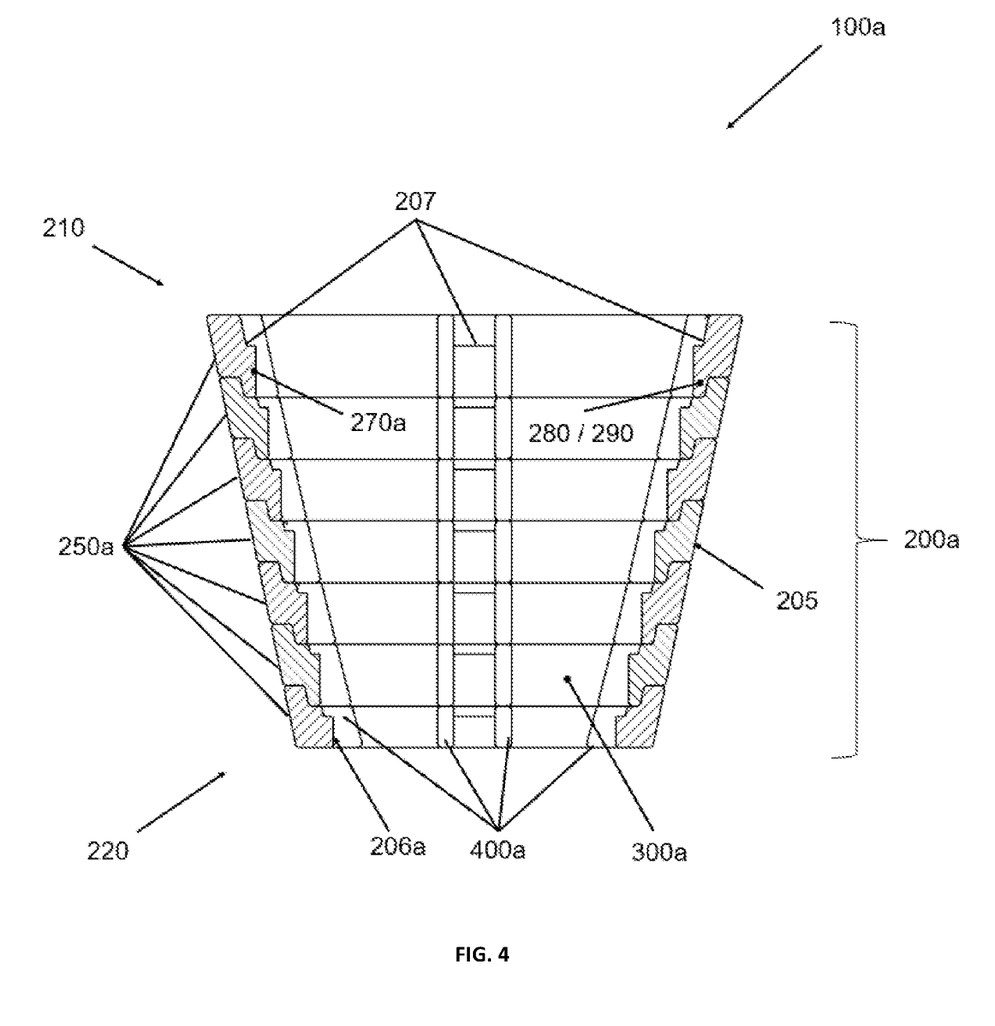

FIG. 4 shows an exemplary second embodiment of an augmentation device 100a. The embodiment according to FIG. 2 largely corresponds to the embodiment described above and shown in FIGS. 1 through 3, so that, to avoid repetition, reference is made to the above description of FIGS. 1 through 3. A structure which is repeated from the description of FIGS. 1 through 3 has the same reference sign. Modifications with respect to the structure shown in FIGS. 1 through 3 have the same reference sign, with an additional letter a.

The cone segments 250a of the embodiment shown in FIG. 4 have stair-like cone notches 207 on the respective inner surface 270a of the cone segment (drawn only for the cone segment 250 at the proximal cone end 210). The cone notches can interact with an applicator (not shown in FIG. 4) in order to ensure better force transmission from the applicator to the augmentation device 100a during implantation in a patient. The cone notches 207 are arranged in the region of the guides 400a—in particular, between the two elevations of a guide 400a—while the rest of the inner surface 270a of the cone segment is smooth.

Figure 5:
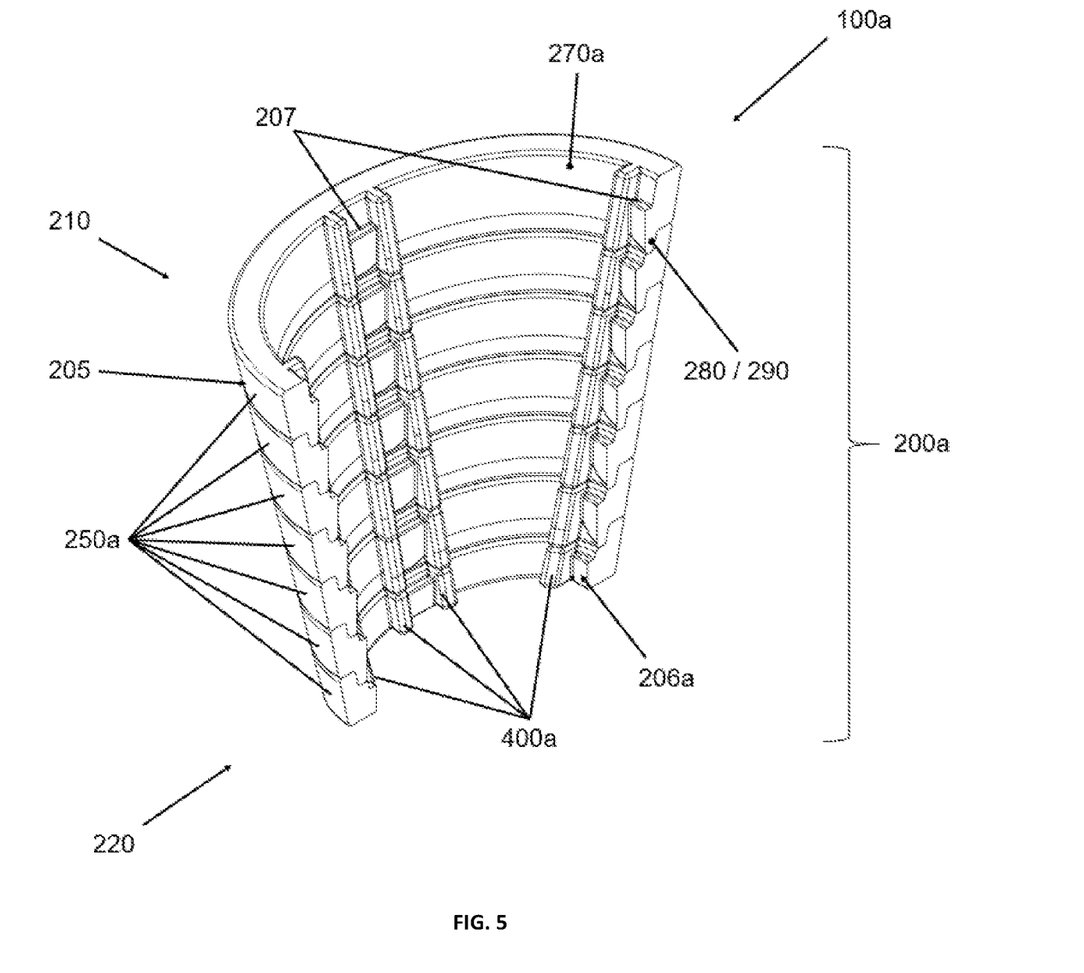

FIG. 5 shows the schematic longitudinal section of the augmentation device 100a from FIG. 4 in a perspective side view. To avoid repetition, reference is made to the above description of FIG. 4.

Figure 6:
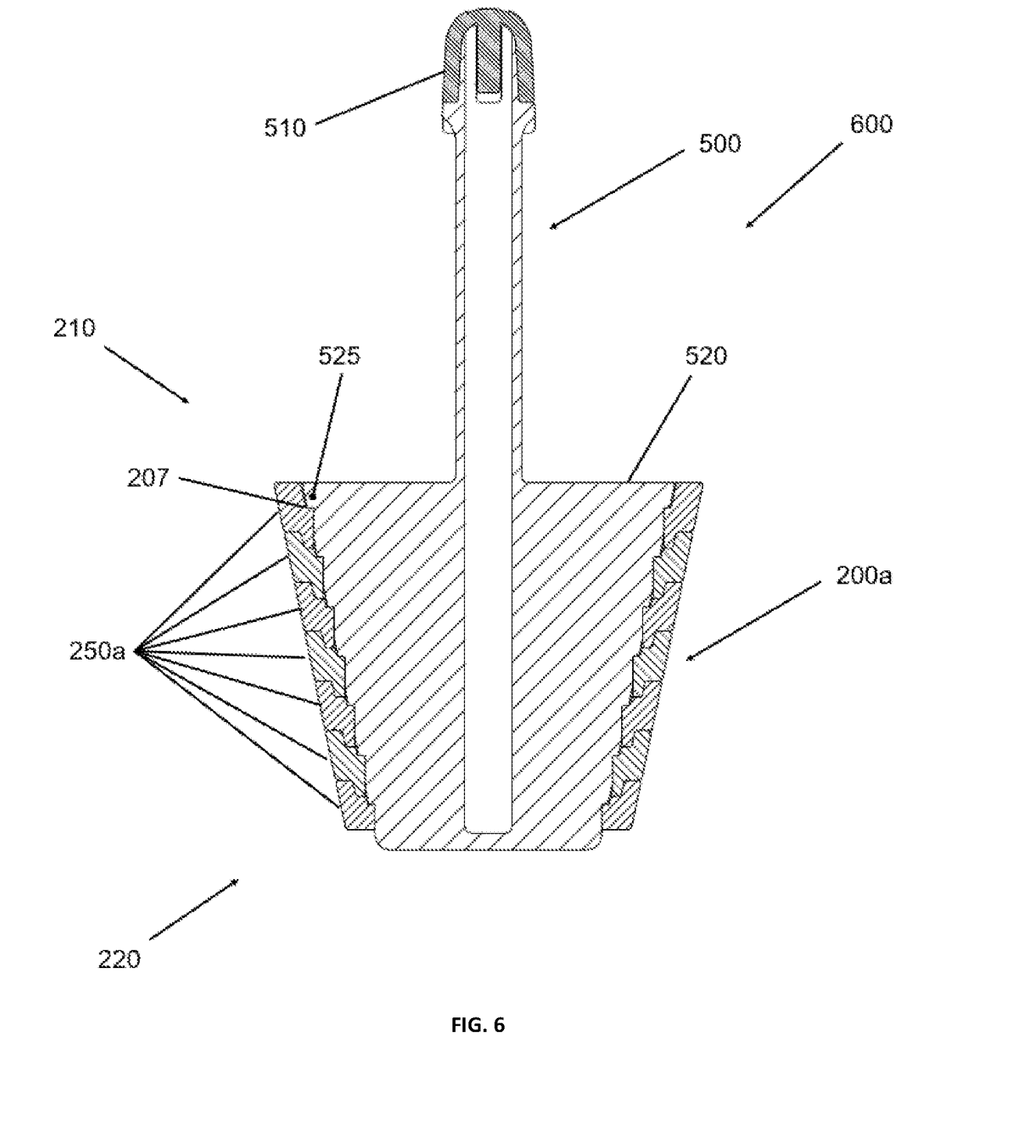

FIG. 6 shows a schematic longitudinal section of an exemplary embodiment of an augmentation system 600. The augmentation system 600 comprises the second embodiment of the augmentation device 100a according to FIGS. 4 and 5 and an applicator 500. To avoid repetition, reference is made to the above description of FIGS. 4 and 5 with respect to the augmentation device 100a.

The applicator 500 comprises a handle 510 for facilitating handling of the augmentation system 600. Furthermore, the applicator 500 comprises a holding element 520 which is connected to the handle 510 and is connected to the augmentation device 100a in a form-fitting and/or force-fitting manner. For this purpose, the applicator 500—in particular, the holding element 520—is inserted into the cone 200a from the proximal cone end 210.

In the embodiment shown, the holding element 520 extends over the entire axial extension of the cone 200a, so that the applicator 500 is in contact with each individual cone segment 250a in the region of the previously described guides 400 (see FIGS. 4 and 5; not shown in FIG. 6), which allows a good introduction of force onto all cone segments 250a during implantation.

In order to improve force transmission from the applicator 500 to the augmentation device 100a during implantation of the same into a patient, the holding element has holding element notches 525—in particular, stair-like holding element notches 525 (drawn only on the section of the holding element 520 facing the proximal cone end 210). The retaining element notches 525 are in form-fitting and/or force-fitting engagement with the cone notches 207. This allows a good application of force from the direction of the proximal cone end 210 to all cone segments 250a and, at the same time, enables a simple release of the augmentation device 100a and applicator 500 after implantation of the augmentation device 100a.

Figure 7:
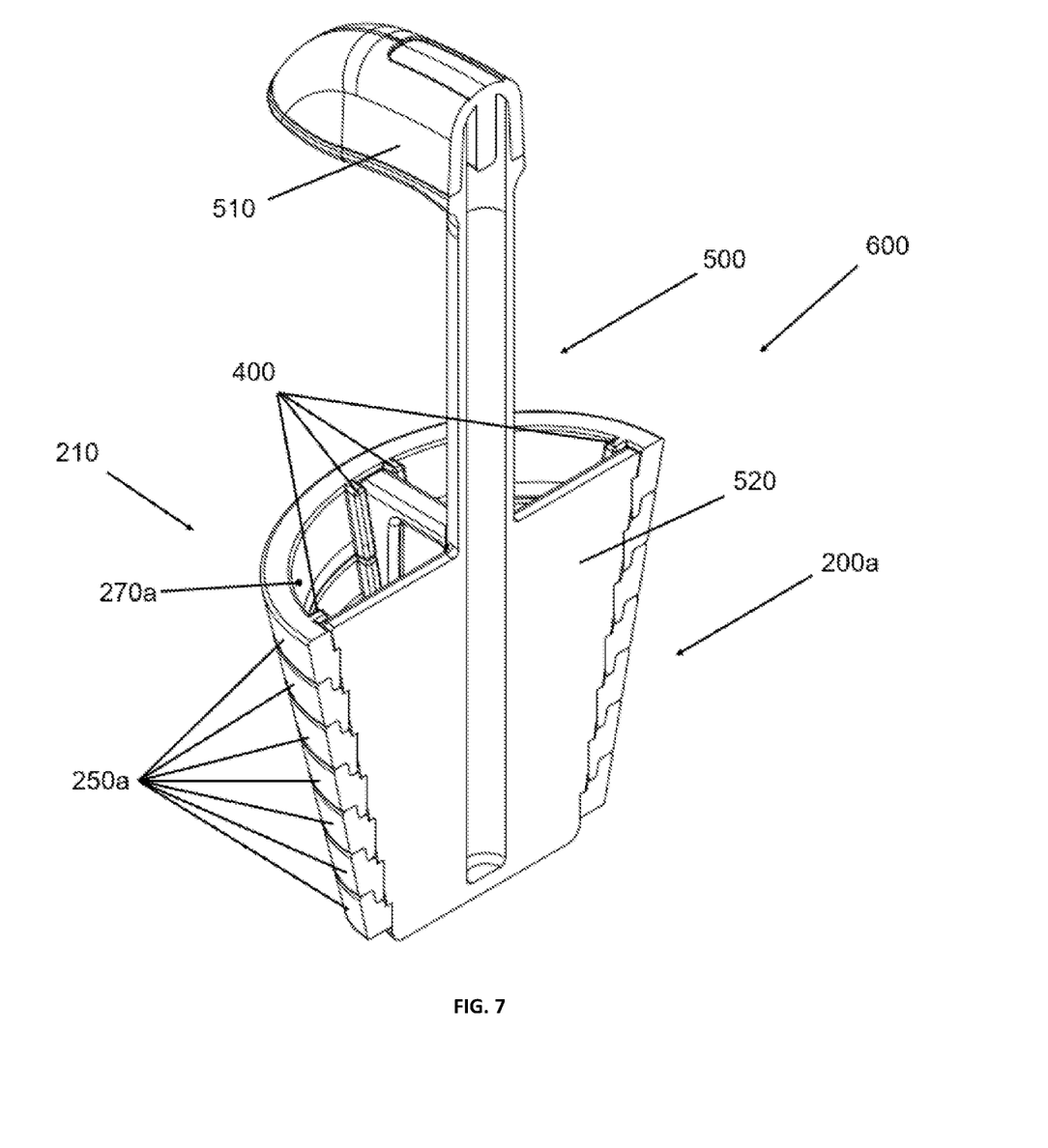

FIG. 7 shows a perspective side view of the schematic longitudinal section of the augmentation system 600 from FIG. 6. To avoid repetition, reference is made to the above description of FIG. 6.

It can be seen in the perspectival side view of FIG. 7 that the holding element 520 comprises four cantilevers which engage in the guides 400 of the cone 200a (only one cantilever is completely visible in the longitudinal section; two cantilevers are visible in the drawing plane. The fourth cantilever is arranged in the cut-off part of the augmentation system 600).

Figure 8:
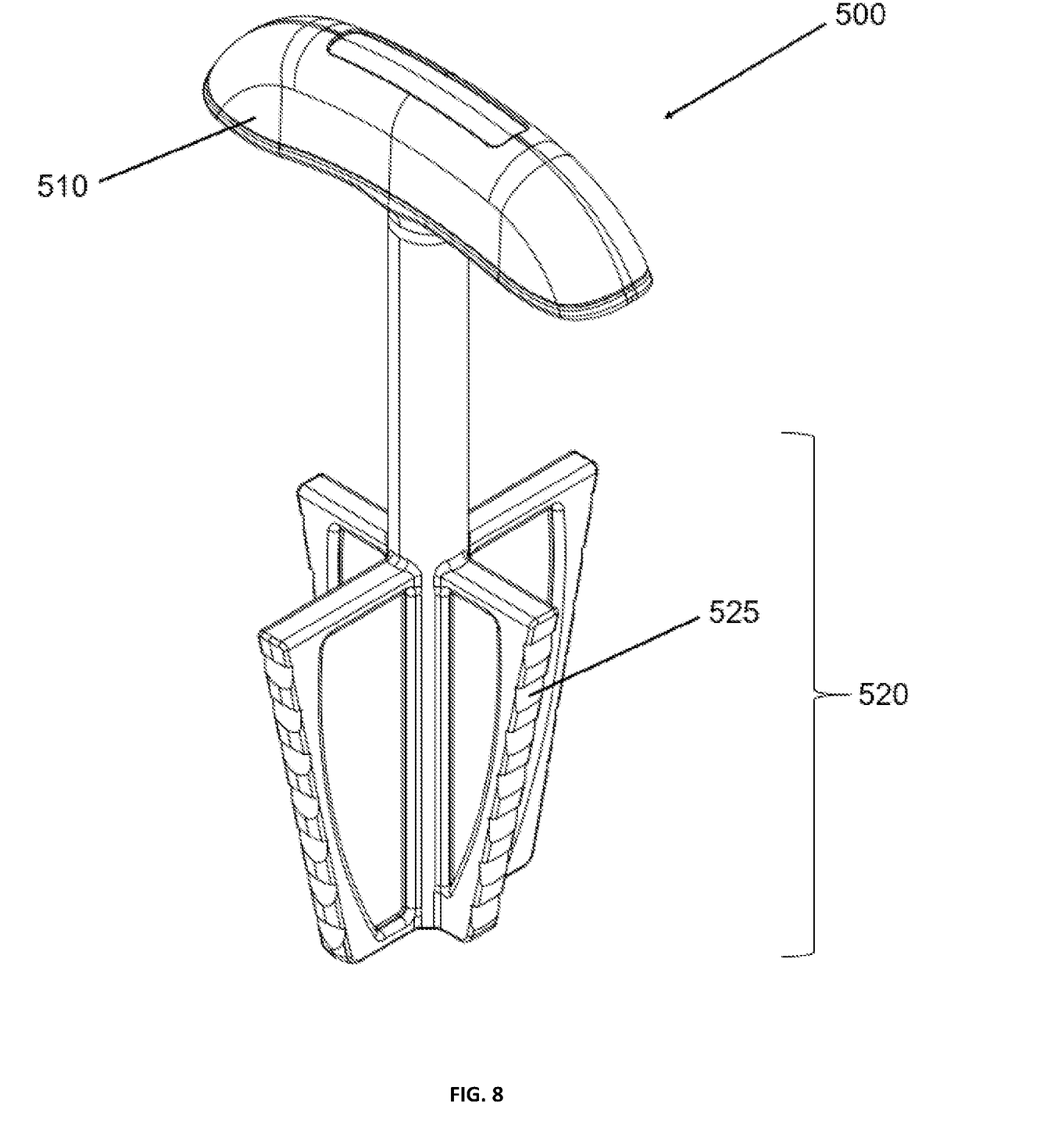

FIG. 8 shows the applicator 500 from FIGS. 6 and 7 in a perspectival side view. To avoid repetition, reference is made to the above description of FIGS. 6 and 7.

On its proximal side facing away from the holding element 520, the handle 510 is designed to be machined with a tool—in particular, a hammer—in order to implant an augmentation device 100, 100a into a patient using pressure.

Figure 9:
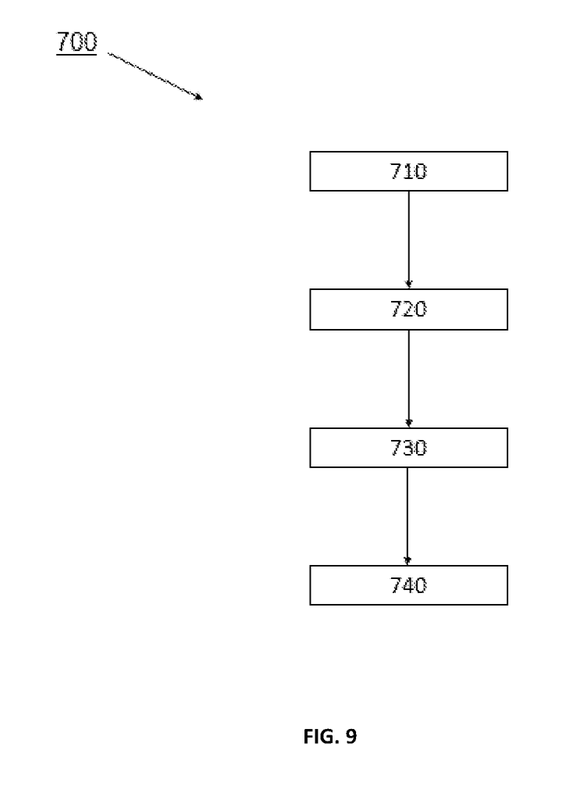

FIG. 9 shows a flow diagram of an implantation method 700 using the augmentation system 600 comprising steps 710 through 740. The augmentation system 600 comprises the augmentation device 100, 100a and the applicator 500. The applicator 500 comprises the handle 510 and the holding element 520 connected to the handle 510. The implantation method 700 serves for implantation of the augmentation device 100, 100a into a bone channel of a patient.

In step 710, the cone size of the augmentation device 100, 100a is adapted to the anatomical conditions of the patient to be treated. This can be done by adding and/or removing cone segments 250, 250a at the proximal cone end 210 and/or at the distal cone end 220. For example, removing the cone segment 250, 250a with the largest cone segment outer diameter 260 at the proximal cone end 210 reduces the maximum outer diameter of the cone and the axial extension of the cone 200, 200a.

In step 720, the applicator 500 is inserted into the channel 300, 300a of the augmentation device 100, 100a in order to reversibly connect the applicator 500 and the augmentation device 100, 100a. As a result of the insertion, the holding element 520 of the applicator 500 comes into contact with the inner surface 206, 206a of the cone—preferably with the inner surface 270, 270a of the cone segment on each individual cone segment 250, 250a—as a result of which, in particular, a form-fitting and/or force-fitting connection is produced.

Step 710 can be performed before or after step 720.

In step 730, the augmentation device 100, 100a is pressed into the bone channel with the aid of the applicator 500. To this end, the user of the augmentation system 600 holds the applicator 500 on the handle 510 and presses the augmentation system 600 with the distal cone end 220 to the fore into the bone channel of the patient. This can be done using pure muscle force or also using a tool, such as a hammer. Step 710—in particular, an addition or removal of a cone segment 250, 250a at the proximal cone end 210—can be carried out before or after step 730.

If the augmentation device 100, 100a is introduced into the bone channel, the applicator 500 is removed from the channel 300, 300a in step 740, and the applicator 500 is thus separated from the augmentation device 100, 100a. Step 710—in particular, an addition or removal of a cone segment 250, 250a at the proximal cone end 210—can be carried out before or after step 740.

REFERENCE SIGNS

100, 100a Augmentation device
200, 200a Cone

205 Cone outer surface
206, 206a Cone inner surface
207 Cone notch
210 Proximal cone end
220 Distal cone end
300 Channel
250, 250a Cone segment
260 Cone segment outer diameter
270, 270a Cone segment inner surface
280 Recess
290 Web
400, 400a Guide
500 Applicator
510 Handle
520 Holding element
525 Holding element notch
600 Augmentation system
700 Implantation method
710 Adapt
720 Insert
730 Press in
740 Remove

What is claimed is:

1. An implantable augmentation device for a joint endoprosthesis comprising:
an annular cone surrounding a channel extending through the cone from a proximal cone end to a distal cone end of the cone, the channel sized and configured to receive and fix a shaft of a joint endoprosthesis,
wherein the cone is formed from a plurality of interconnected annular cone segments, wherein a cone segment outer diameter of the individual cone segments decreases from the proximal cone end to the distal cone end,
wherein the cone segments are each designed in the form of a closed ring,
wherein at least some of the plurality of cone segments have a circumferential web arranged on an inner surface of the cone segment facing the channel,
wherein at least some of the plurality of cone segments have a circumferential recess arranged on the inner surface of the cone segment facing the channel,
wherein the circumferential recess and the circumferential web of two adjacent cone segments in the annular cone interact in order to connect the two adjacent cone segments in the annular cone to one another,
wherein the cone segments are designed to be separable from one another, so that the cone has an adaptable cone size,
wherein the cone segments are interconnected along a longitudinal axis of the annual cone in a form-fitting and/or force-fitting manner such that they are configured to be disconnected from and reconnected to each other.

2. The augmentation device according to claim 1, wherein the cone segments are reversibly separable from one another.

3. The augmentation device according to claim 1, wherein the cone segments are interconnected by means of a tongue-and-groove connection.

4. The augmentation device according to claim 1, wherein the cone has a smooth conical outer surface facing away from the channel.

5. The augmentation device according to claim 1, wherein the cone segments each have a guide in order to reversibly connect the cone to an applicator.

6. The augmentation device according to claim 5, wherein the guide faces the channel such that the applicator can be reversibly connected to the cone by being inserted into the channel.

7. The augmentation device according to claim 1, wherein the cone segments comprise a polymer, a metal, and/or a metal alloy.

8. An augmentation system comprising the augmentation device according to claim 1 and an applicator, the applicator comprising:
a handle and a holding element connected to the handle, wherein the holding element is shaped such that, when the applicator is inserted into the channel of the cone, the holding element rests against an inner surface of the cone and thus reversibly connects the augmentation device and the applicator to one another.

9. The augmentation system according to claim 8, wherein the applicator can be inserted into the channel from the proximal cone end.

10. The augmentation system according to claim 8, wherein, on the holding element, holding element notches are formed, which can be brought into engagement with cone notches on the inner surface of the cone.

11. An implantation method into a bone channel by means of the augmentation system according to claim 8, comprising the steps of:
a. adapting the cone size of the augmentation device;
b. inserting the applicator into the channel of the augmentation device;
c. pressing the augmentation device into the bone channel by means of the applicator; and,
d. removing the applicator from the channel of the augmentation device.

* * * * *